United States Patent [19]

Poli et al.

[11] Patent Number: 5,110,936

[45] Date of Patent: May 5, 1992

[54] PROCESS FOR THE PREPARATION OF 3-(LPYROGLUTAMYL)-L-THIAZOLIDINE-4-CARBOXYLIC ACID DERIVATIVES

[75] Inventors: Stefano Poli; Lucio Del Corona, both of Milan, Italy

[73] Assignee: Poli Industria Chimica S.P.A., Milan, Italy

[21] Appl. No.: 594,313

[22] Filed: Oct. 9, 1990

[30] Foreign Application Priority Data

Oct. 12, 1989 [IT] Italy ................ 22003 A/89

[51] Int. Cl.$^5$ ................ C07D 277/04; C07D 277/18; C07D 207/00
[52] U.S. Cl. .................. 548/200; 548/201; 548/537
[58] Field of Search ............ 548/200, 201, 537

[56] References Cited

PUBLICATIONS

Chemical Abstracts, vol. 107: 198361n Pyroglutamide derivatives, procedure for their preparation, and their use as nootropics, Kimura et al. 1987.
Organic Chem. 2nd Ed., McMurry, p. 754, 1988.
CA vol. 113: 55406u Chromatographic ... molecules, Schneider, 1989.
CA vol. 112: 34440g Electrically ... culture, Schneider, 1989.

Primary Examiner—Mary C. Lee
Assistant Examiner—Joseph K. McKane
Attorney, Agent, or Firm—Walter H. Schneider

[57] ABSTRACT

3-(L-pyroglutamyl)-L-thiazolidine-4-carboxylic acid and derivatives thereof are prepared by condensing L-pyroglutamic acid or its substitution products, either in the presence of dicyclohexylcarbodiimmide or the like, or by condensation of active derivatives of L-pyroglutamic acid with 4-thiazolidine-carboxylic acid derivatives.

5 Claims, No Drawings

PROCESS FOR THE PREPARATION OF 3-(L-PYROGLUTAMYL)-L-THIAZOLIDINE-4-CARBOXYLIC ACID DERIVATIVES

DISCLOSURE

The present invention relates to a process for the preparation of L-pyroglutamic acid or the derivatives thereof.

Italian Pat. No. 1.202.426 disclosed L-thiazolidine-4-carboxylic acid, having immuno-modulating, antitoxic, antiinflammatory, antioxidating and antiageing activities, which compound is prepared starting from an L-pyroglutamic acid reactive ester or from the acid chloride and L-thiazolidine-4-carboxylic acid.

More particularly, said process involves the use, for instance, either of reactive esters of L-pyroglutamic acid with pentachlorophenol, pentafluorophenol, 2,4,5-trichlorophenol, N-hydroxysuccinimide, N-hydroxyphthalimide, which are reacted with L-thiazolidine-4-carboxylic acid in aprotic solvents, in the presence of tertiary bases, or of L-pyroglutamic acid chloride which is reacted with L-thiazolidine-4-carboxylic acid in alkali medium.

Italian Pat. application No. 19.401 A/89 disclosed 3-(L-pyroglutamyl)-L-thiazolidine-4-carboxylic acid derivatives having the same pharmacological properties, which derivatives are prepared according to quite analogous processes, starting from L-pyroglutamic acid reactive esters or amides and alcohols or amines.

Said processes suffer from some disadvantages, e.g. use of toxic substances such as halophenols, poor stability of L-pyroglutamic acid esters with N-hydroxysuccinimide and N-hydroxyphthalimide, unsatisfactory yields, high instability and difficulty in handling of L-pyroglutamyl chloride.

The process of the present invention allows to overcome the above mentioned disadvantages, to obtain these compounds more easily, in higher yields and with no use of toxic and/or unstable intermediates.

The process of the invention comprises reacting a compound of formula (I)

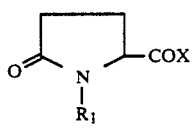

(I)

wherein :
R$_1$ is hydrogen, C$_1$–C$_6$ alkyl C$_3$–C$_7$ cycloalkyl, C$_4$–C$_{10}$ cycloalkylalkyl, aryl and substituted aryl, C$_2$–C$_5$ alkoxycarbonyl, C$_2$–C$_{10}$ alkylcarbonyl, arylcarbonyl and aralkylcarbonyl, and C$_8$–C$_{13}$ aralkoxycarbonyl and substituted aralkoxycarbonyl; and X is OH, Cl or OR$_2$ wherein R$_2$ is an activating group, with a compound of formula (II)

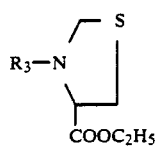

(II)

wherein :

R$_3$ is hydrogen or C$_3$–C$_9$ trialkylsilyl, with the proviso that when X is OH the reaction is carried out in the presence of usual condensing agents, such as dicyclohexylcarbodiimide, diisopropylcarbodiimide or basic carbodiimides, in aprotic solvents such as dioxane, tetrahydrofuran, ethyl acetate, dimethylformamide, dimethylsulfoxide, dichloromethane, hexamethylphosphoric triamide or mixtures thereof, to give a 3-(L-pyroglutamyl)-L-thiazolidine-4-carboxylic acid derivative of formula (III)

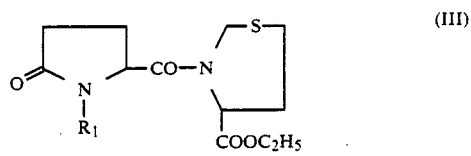

(III)

wherein R$_1$ has the above mentioned meanings, which derivative (III) can possibly be transformed into 3-(L-pyroglutamyl)-L-thiazolidine-4-carboxylic acid in very good yields, under mild acid or basic hydrolysis conditions.

In particular it has been surprisingly found that only the ethyl ester of L-thiazolidine-4-carboxylic acid allowed to obtain very good yields whereas other esters such as the methyl- or isopropyl esters gave poor results. The favourable effect of the ethyl ester II is independent on the kind of pyroglutamic acid derivative of formula I.

The following examples further illustrate the invention.

EXAMPLE 1

A solution of 16.78 g (0.084 mole) of ethyl L- thiazolidine-4-carboxylate hydrochloride in 33 ml of water is treated with 16.78 g of potassium carbonate and extracted with 40 ml of ethyl acetate. The organic phase is dried over sodium sulfate, filtered and diluted to 85 ml with ethyl acetate. The solution is stirred and cooled to 0°–5° C., then 19.2 g (0.093 mole) of dicyclohexylcarbodiimide dissolved in 20 ml of ethyl acetate and 12 g (0.093 mole) of L-pyroglutamic acid are added thereto. The reaction mixture is stirred for 1 hour at 0°–5° C., then 12 hours at room temperature, dicyclohexylurea is filtered, the filtrate is evaporated under vacuum and the oily residue, consisting in ethyl 3-(L-pyroglutamyl)-L-thiazolidine-4-carboxylate is taken up into 25 ml of water. 3.73 g of sodium hydroxide dissolved in 13.3 ml of water are dropped into the resulting solution. After 30 minutes, the reaction mixture is acidified with concentrated hydrochloric acid at 0°–5° C, kept for 2 hours at 5° C, then filtered washing with little cool water and dried to obtain 17.8 g (87.6%) of 3-(L-pyroglutamyl)-L-thiazolidine-4-carboxylic acid, m.p. 193°–194° C.

EXAMPLE 2

23 g (0.1 mol) of L-N-t-butoxycarbonylpyroglutamic acid (E. Schröder and E. Klinger, Ann. Chem., 673, 1964, 202) and 16.1 g (0.1 mol) of ethyl L- thiazolidine-4-carboxylate are dissolved in 150 ml of THF, to the solution stirred at 0°–5° C., 21 g (0.105 mol) of dicyclohexylcarbodiimide are added and the slurry is stirred for 15 hours at room temperature. The dicyclohexylurea is filtered, the wear filtrate is evaporated u.v. and the oily residue is kept in 40 ml of water. In the solution 6.6 g of potassium hydroxyde in a little water are dropped in 30' at 15°–20° C., the pH L is adjusted to 2 with hydrochloric acid at 0°–5° C. and after 2 hours the precipitated L-pyroglutamyl-L- thiazolidine-4-carboxylic acid is filtered and dried, giving 88%, mp. 193°–4°.

In the Table I are summarized the results obtained by the use of the methyl, n-propyl and iso-propyl esters of L-thiazolidine-4-carboxylic acid in the same conditions of examples 1 and 2.

TABLE I

| Ester of thiazo-lidine-4-carboxylic acid | Example | Yield (%) | Example | Yield (%) |
| --- | --- | --- | --- | --- |
| methyl | 1 | 43 | 2 | 23 |
| n-propyl | 1 | 38 | 2 | 31 |
| i-propyl | 1 | 51 | 2 | 44 |

We claim:

1. A process for the preparation of 3-(L-pyroglutamyl)-L-thiazolidine-4- carboxylic acid and its derivatives which process comprises reacting a compound of formula (I)

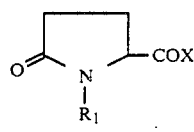

wherein:

$R_1$ is hydrogen, $C_1$–$C_6$ alkyl, $C_3$–$C_7$ cycloalkyl, $C_4$–$C_{10}$ cycloalkylalkyl, aryl and substituted aryl, $C_2$–$C_5$ alkoxycarbonyl, $C_2$–$C_{10}$ alkylcarbonyl, arylcarbonyl and aralkylcarbonyl, $C_8$–$C_{13}$ aralkoxycarbonyl and substituted aralkoxycarbonyl; and X is OH, with a compound of formula (II)

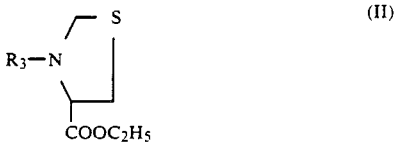

wherein $R_3$ is hydrogen or $C_3$–$C_9$ trialkylsilyl in the presence of a condensing agent.

2. A process according to claim 1, wherein the condensing agent is selected from the group consisting of dicyclohexylcarbodiimide and carbonyldiimidazole.

3. A process according to claim 1 in which $R_1$ is selected from hydrogen and $C_2$–$C_5$ alkoxycabonyl.

4. A process according to claim 1 in which the compound of formula (I) is L-pyroglutamic acid.

5. A process according to claim 1 in which the compound of formula 1 is L-N-t-butoxycarbonylpyroglutamic acid.

* * * * *

UNITED STATES PATENT AND TRADEMARK OFFICE
CERTIFICATE OF CORRECTION

PATENT NO. : 5,110,936
DATED : May 5, 1992
INVENTOR(S) : Stefano Poli; Lucio Del Corona It is certified that error appears in the above-identified patent and that said Letters Patent is hereby corrected as shown below:

On title page, item [54] and col. 1, line 2, "LPYROGLUTAMYL" should read ---L-PYROGLUTAMYL---

Signed and Sealed this

Thirteenth Day of July, 1993

Attest:

MICHAEL K. KIRK

Attesting Officer

Acting Commissioner of Patents and Trademarks